United States Patent [19]

Nobbio

[11] Patent Number: Plant 6,162

[45] Date of Patent: Apr. 26, 1988

[54] CARNATION NAMED MEI-BAO

[76] Inventor: Giacomo Nobbio, Strada Villetta 12, San Remo, Imperia, Italy

[21] Appl. No.: 841,882

[22] Filed: Mar. 20, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler; W. Dennis Drehkoff

[57] ABSTRACT

A new variety of carnation of the closed calyx or non-splitting type, characterized by a vigorous growth and precocious blooming habit of very large flowers having dark red and violet coloration of its petals which are bordered by white margins.

1 Drawing Sheet

BACKGROUND OF THE NEW PLANT

This new carnation variety is the result of breeding efforts carried on at San Remo, Italy, with the object of producing a new carnation having flowers of a distinctive coloration and good quality borne on a plant having a vigorous and upright growth habit and excellent flower production. The new plant originated as a seedling produced by crossing of selected individually-identified carnations growing among my collection of distinctive plants maintained at San Remo for breeding purposes. This particular seedling was selected for propagation and tests because of its distinctive colorations and apparent profuse production of buds and flowers. This new plant was asexually reproduced by means of cuttings at San Remo under my direction through successive generations and the distinctive characteristics of this plant have been found to hold true from generation to generation and appear to be firmly fixed.

DESCRIPTION OF THE DRAWING

My new variety of carnation plant is illustrated by the accompanying full color photographic drawing, which shows a group of flowering stems having buds in various stages of opening, nearly opened flowers and blooms in further stages of maturity, the flower coloration being shown as nearly true as it is reasonably possible to obtain by means of conventional photographic procedures.

DESCRIPTION OF THE NEW PLANT

The following is a detailed description of my new carnation variety, based upon observation of the plants grown under conventional greenhouse practices, with color designations being according to the R.H.S. Colour Chart published by The Royal Horticultural Society of London, England.

THE PLANT

Origin: Seedling.
Parentage:
- *Seed parent.*—Stock plant 782.
- *Pollen parent.*—Stock plant 813.

Classification:
- *Botanic.*—*Dianthus chinensis.*
- *Commercial.*—Greenhouse carnation for cut flowers— Chinese.

Form: Bush.
Height: About 60 cm to 70 cm.
Growth: Vigorous and upright with good strength.
Branching: Normal.
Foliage:
- *Quantity.*—Abundant.
- *Leaf size.*—Short.
- *Leaf shape.*—Normal.
- *Margin type.*—Entire.
- *Texture.*—Smooth.
- *Color.*—Upper side — dark green; Under side — dark green.

THE BUD

Size: Small, about 1.5 cm depth and 2 cm long.
Form: Cylindrical, pointed, urn-shaped.
Opening rate: Medium.
Color:
- *When sepals first divide.*—RHS 66 A.
- *When petals begin to unfurl.*—RHS 75/B.

Calyx:
- *Size.*—Long.
- *Shape.*—Pear shaped.
- *Aspect.*—Hairy.
- *Splitting.*—The calyx does not split.

Sepals:
- *Condition.*—Upstanding.
- *Color.*—Inside — pale green. Outside — green.

Peduncle: Short and erect.

THE FLOWER

Blooming habits: Continuous and profuse.
Size of bloom: Small.
- *Diameter.*—About 3.5 to 5 cm.
- *Depth.*—About 1 cm.

Borne: Singly.
Shape: Flattened cupule in full bloom.
Petalage:
- *Number of petals.*—About 44–55.
- *Arrangement.*—Generally imbricated.
- *Form.*—Irregularly indented, Type I UPOV.
- *Color.*—Outer petal/floret, body: RHS 66/A. Base: RHS 59/A. Reverse side: RHS 155/D. Inside petal/floret, body: RHS 155/D. Base: RHS 142/D. Reverse side: RHS 142/D. Margin: RHS 155/D.

Appearance: Velvety.
Texture: Soft.
Peduncle:

*Length.*—About 1.5–2.5 cm.
*Color.*—Pale green.
*Persistence.*—The flowers hang on and dry.
*Fragrance.*—Absent.
*Lasting quality.*—On the plant, good; as a cut flower, good.

REPRODUCTIVE ORGANS

Stamens:
*Number.*—8–12.
Anthers:
*Size.*—Normal.
*Color.*—Pale Violet RHS 85/A.
Filaments:
*Length.*—1.5 cm.
*Color.*—White.
Pollen:
*Color.*—Pale violet.
Pistils:
*Number.*—Two.
Styles:
*Length.*—1 cm.
*Color.*—White.

Stigmas:
*Color.*—White.
Ovaries: Ovoid shaped.
*Texture.*—Smooth.
Fruit: Fertile, ovoid shaped.

This new variety of carnation plant is distinguishable from commercially-available varieties and in particular from the "Mei-Schiang" variety by its paler basic color, by the more jagged margin of its petals. The multicolored flower is borne on a relatively short, strong peduncle. The flower has a closed calyx which does not split, and the plant has an excellent capacity for continuous and profuse production of blooms which is essential for the cut flower market.

I claim:

1. A new and distinct variety of carnation plant, substantially as herein shown and described, characterized by its high productivity of very large flowers borne singly on rigid generally upright pedicels on a sturdy, upright relatively short peduncle, the flowers being characterized by having dark red and violet coloration of its petals which are bordered by a white margin.

* * * * *

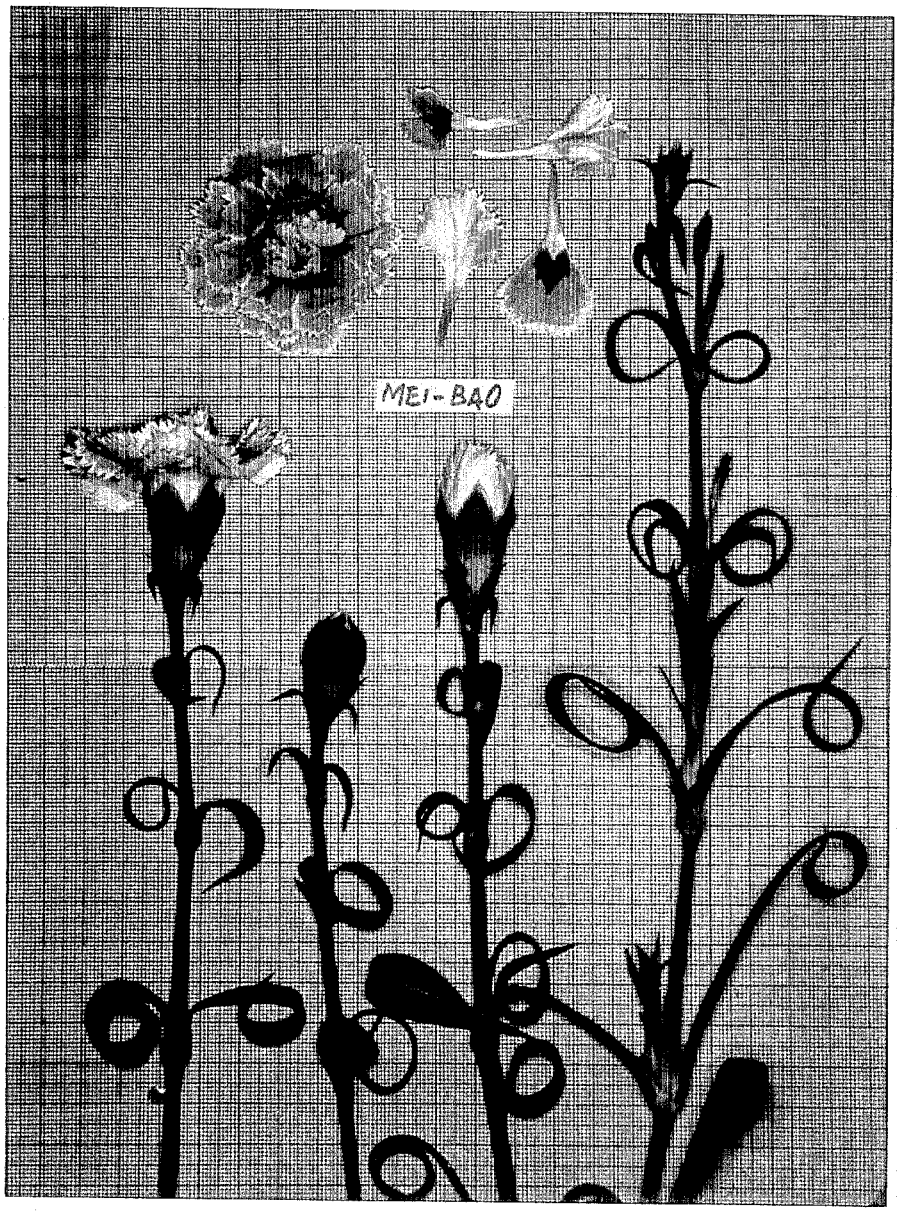
MEI-BAO